United States Patent [19]

Lang, Jr. et al.

[11] 4,259,504

[45] Mar. 31, 1981

[54] SUBSTITUTED 1H-1,2,4-TRIAZOLES

[75] Inventors: Stanley A. Lang, Jr., Stony Point; Yang-I Lin, Nanuet; David N. Ridge, Grandview, all of N.Y.

[73] Assignee: American Cyanamid Company, Stamford, Conn.

[21] Appl. No.: 69,671

[22] Filed: Aug. 27, 1979

[51] Int. Cl.³ .................... A61K 31/41; A61K 31/44; C07D 249/08; C07D 401/04
[52] U.S. Cl. .................................. 548/262; 424/250; 424/263; 424/269; 544/405; 546/276; 548/269
[58] Field of Search ............................... 548/262, 269

[56] References Cited

U.S. PATENT DOCUMENTS 4,038,405  7/1977  Evans et al. ........................ 548/269
4,151,169  4/1979  Sale et al. ............................ 548/262

OTHER PUBLICATIONS

Jackson et al., Chemical Abstracts, vol. 45, columns 6699–6700, (1951).

Primary Examiner—Alton D. Rollins
Attorney, Agent, or Firm—Edward A. Conroy, Jr.

[57] ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the novel active ingredients of said compositions of matter being certain substituted 1-phenyl-1H-1,2,4-triazoles and/or the pharmacologically acceptable acid-addition salts thereof.

9 Claims, No Drawings

SUBSTITUTED 1H-1,2,4-TRIAZOLES

BRIEF SUMMARY OF THE INVENTION

This invention relates to new organic compounds and, more particularly, is concerned with novel substituted 1-phenyl-1H-1,2,4-triazoles which may be represented by the following structural formula:

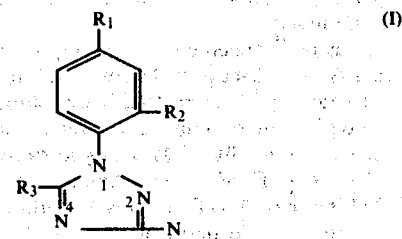

wherein $R_1$ and $R_2$ are each individually selected from the group consisting of hydrogen, fluoro, chloro, bromo, nitro, amino, and dimethylaminomethyleneamino; $R_3$ is selected from the group consisting of 2-pyridyl, 3-pyridyl, 4-pyridyl, 2-pyrazinyl, 3,4,5-trimethoxyphenyl and moieties of the formula:

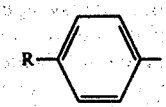

wherein R is hydrogen, fluoro, chloro, bromo, nitro, amino or dimethylaminomethyleneamino with the proviso that when R is hydrogen then $R_1$ and $R_2$ may not both be hydrogen; and $R_4$ is hydrogen or methyl.

The organic bases of this invention form non-toxic acid-addition salts with a variety of pharmacologically acceptable organic and inorganic salt-forming reagents. Thus, acid-addition salts, formed by a mixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme:

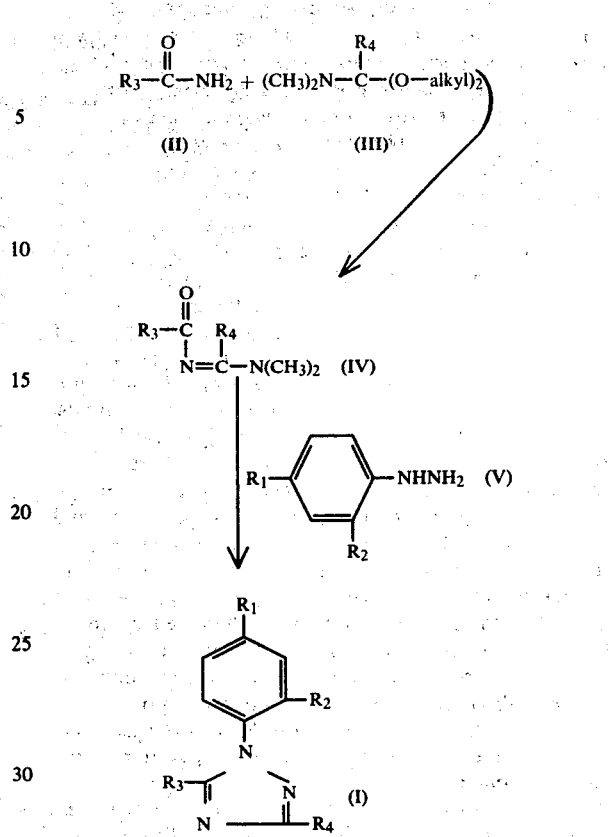

wherein alkyl is methyl or ethyl and $R_1$, $R_2$, $R_3$ and $R_4$ are as hereinabove defined. In accordance with the above reaction scheme, an amide (II) such as picolinamide, nicotinamide, isonicotinamide, pyrazinamide or an appropriately substituted benzamide is condensed with the dimethylacetal or diethylacetal of either dimethylformamide or dimethylacetamide (III). This condensation is best carried out in an inert solvent such as dimethylformamide or dimethylacetamide at 100°–120° C. for a period of 1–3 hours to provide the corresponding substituted N-dimethylaminomethylene-amide (IV). Treatment of (IV) with an appropriately substituted phenylhydrazine (IV) in a solvent such as glacial acetic acid at 75°–100° C. for a period of 1–3 hours then provides the novel compounds (I) of the present invention. Compounds having a nitrophenyl substituent may be converted to the aminophenyl derivative by treatment with sodium sulfide in aqueous dioxane at 80°–100° C. for a period of 1–4 hours followed by precipitation with water and recrystallization from an organic solvent. Treatment of the aminophenyl derivative with excess dimethylformamide dimethylacetal at the reflux temperature for 1–3 hours then provides the corresponding dimethylaminomethyleneamino derivative.

The novel compounds of the present invention have been found to be highly useful for meliorating inflammation and inhibiting joint deterioration in mammals when administered in amounts ranging from about one milligram to about 250 mg./kg. of body weight per day. A preferred dosage regimen for optimum results would be from about 5 mg. to about 100 mg./kg. of body weight per day, and such dosage units are employed that a total of from bout 0.35 g. to about 7.0 g. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered by the oral route or by intravenous, intramuscular, topical or subcutaneous routes.

Compounds according to the present invention may be orally administered, for example, with an inert diluent or with an assimible edible carrier, or they may be enclosed in hard or soft gelatin capsules, or they may be compressed into tablets, or they may be incorporated directly with the food of the diet. For oral therapeutic administration, the active compounds may be incorporated with excipients and used in the form of tablets, troches, capsules, suspensions and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions in such that a suitable dosage will be obtained. Preferred compositions or preparations according to the present invention are prepared so that an oral dosage unit form contains between about 50 to 250 mg. of active compound.

The tablets, troches, pills, capsules and the like may also contain the following: a binder such as gum tragacanth, acacia, corn starch or gelatin; excipients such as dicalcium phosphte; a disintegering agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A suspension may contain the active ingredient, sucrose as a sweetening agent, methyl and propyl parabens as preservatives, a dye and flavoring such as cherry or orange flavor. Of course, any material used in preparing any dosage unit form should be pharmaceutically pure and substantially non-toxic in the amounts employed.

Compositions according to the present invention having the desired clarity, stability and adaptability for parenteral use are obtained by dissolveing from 0.10% to 10.0% by weight of active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecule weight of from about 200 to about 400.

In addition to the active compound, the parenteral solutions may contain various preservatives which may be used to prevent bacterial and fungal contamination. Such preservatives are, for example, myristyl-gamma picolinium chloride, phenyl mercuric nitrate, benzalkonium chloride, phenethyl alcohol, p-chlorophenyl--glycerol ether, methyl and propyl parabens and thimerosal. As a practical matter, it is alxo convenient to employ antioxidants. Suitable antioxidants include, for example, sodium bisulfite, sodium metabisulfite and sodium formaldehyde sulfoxylate. Generally, from about 0.05 to about 0.2% concentrations of antioxidant are employed.

Adjuvant induced experimental polyarthritis is a specific systemic disease of the rat which shares interesting similarities with rheumatoid arthritis. Specifically, the histology of the two diseases bears a remarkable resemblence as shown by C. M. Pearson, et al, Am. J. Path., 42, 73 (1963). E. M. Glenn, Am. J. Vet. Res., 27, (116), 339 (1966) has classified adjuvant induced polyarthritis as a crippling and permanent deformity resulting from diffuse connective tissue involvement around certain susceptible joints in the rat. Zahiri, et al., Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri, et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong, et al., J. Pharm. & Exp. Ther., 185, 127 (1973) and G. R. Bobalic, et al., Agents and Actions, 4, 364 (1974)]. The most pointed reference showing the relationship between arthritis and joint deterioration is "An X-Ray Analysis of Adjuvant Arthritis in the Rat; the Effect of Prednisolone and Indomethacin", Blackham, et al., Agents and Action, 7 (No. 1), 145-151 (1977). In a similar manner, inhibition of the progress of arthritis in paws of rats treated with the compounds of this invention also lessens associated joint deterioration.

The novel compounds of the present invention are active anti-inflammatory agents as established in the following tests:

Adjuvant Arthritis Assay

Groups of three Royal Hart Wistar strain rats, weighing 200±10 g. each were injected intradermally in the right hand paw with Freund's adjuvant (dried human tubercle bacilli in a mineral oil vehicle) at a dose of 2 mg./kg. of body weight. Test compounds were administered orally in a 1.5% starch vehicle at 50 mg./kg. of body weight once daily on days 0 through 13 post-challenge. Control rats were treated in a similar manner, buty given only starch vehicle. On the 14th day post-challenge the diameter of the injected paw (primary lesion) was measured by micrometer caliper. From these measurements of inflamed paws a deterioration was made of the relative surface area (RSA). This is a ratio of the mean surface area of the paws of 3 treated rats/mean surface area of the paws of 60 control rats. If the RSA is equal to or less than 0.76, the compound is retested. After the second test, the mean RSA for the rat paws from both tests is calculated and if it is equal to or less than 0.736 the compound is tested a third time. If the mean RSA of all three tests is less than 0.753, the compound is considered active. The results of this test with typical compounds of this invention appear in Table I below.

TABLE I

| Compound | Result |
| --- | --- |
| 1-Phenyl-5-(p-nitrophenyl)-1H-1,2,4-triazole | Active |
| 1-(p-Fluorophenyl)-5-(p-nitrophenyl)-1H-1,2,4-triazole | Active |
| 1-(p-Bromophenyl)-5-(p-nitrophenyl)-1H-1,2,4-triazole | Active |
| 5-(p-Aminophenyl)-1-(p-bromophenyl)-1H-1,2,4-triazole | Active |
| 5-(p-Aminophenyl)-1-(p-fluorophenyl)-1H-1,2,4-triazole | Active |
| 5-[p-(Dimethylaminomethylene)amino]-1-(p-fluorphenyl)-1H-1,2,4-triazole | Active |
| 5-(p-Aminophenyl)-1-(p-chlorophenyl)-1H-1,2,4-triazole | Active |
| 5-(p-Fluorophenyl)-1-(p-nitrophneyl)-1H-1,2,4-triazole | Active |
| 1-(p-Aminophenyl)-5-(p-fluorophenyl)-1H-1,2,4-triazole | Active |
| 5-(p-Aminophenyl)-1-(o-fluorophenyl)-1H-1,2,4-triazole | Active |
| 2-Cyano-4'-[1-(p-fluorophenyl)-1H-1,3,4-triazol-5-yl]acetanilide | Active |

Carrageenin Edema Assay

Royal Hart, Wistar strain rats ranging in weight from 80 to 90 grams were used. The rats were fasted overnight prior to dosing but had free access to water. The test compounds were administered in aqueous suspension, by gavage, in a volume of 1.7 ml. per 50 grams of rat [corresponds to hydration volume used by Winter, et al., Proc. Soc. Exp. Biol & Med., 111, 544–547 (1962)]. The dose of all compounds was 250 mg./kg. The phlogistic agent used was carrageenin prepared as a sterile 1% suspension in 0.9% aqueous sodium chloride for routine testing. A volume of 0.05 ml. was injected into the plantar tissue of the right hind paw. Measurements were made 5 hours after drug administration (4 hours after carrageenin challenge). The paw of the unanesthetized rat was immersed in mercury exactly to an ink mark on the skin over the lateral malleolus. The mercury was contained in a glass cylinder 25×60 mm. The mercury column was connected with a Statham pressure transducer (model P23BB), range 0–5 cm. mercury. The output from the transducer was led through a model 260BLH signal conditioning unit and visualized by digital indicator. Volumes of both the normal and carrageenin inflamed test were determined. The difference between the two measurements was considered to be the increased edema due to the carrageenin administration. Results were expressed as a control (C)/treated (T) efficacy ratio. (The ratio of mean edema volume of 8 control rats over the mean edema volume of 2 treated rats.) If the C/T ratio is equal to or greater than 1.41, the test is repeated. If the mean ratio of test 1 and 2 is equal to or greater than 1.43, the compound is considered active. The results of this test with typical compounds of this invention are recorded in Table II below.

TABLE II

| Compound | Result |
| --- | --- |
| 3-(4H-1,2,4-Triazol-3-yl)-pyridine | Active |
| 2-[1-(p-Chlorophenyl)-1H-1,2,4-triazol-5-yl]-pyrazine | Active |
| 4-(1-Phenyl-1H-1,2,4-triazol-5-yl)-pyridine | Active |
| {1-[p-(Difluoromethylsulfonyl)-phenyl]-1H-1,2,4-triazol-5-yl}-pyrazine | Active |
| 1,5-Diphenyl-1H-1,2,4-triazole | Active |
| 1-(p-Bromophenyl)-3-methyl-5-(3,4,5-trimethoxyphenyl)-1H-1,2,4-triazole | Active |
| [1-(p-Nitrophenyl)-1H-1,2,4-triazol-5-yl]-pyrazine | Active |
| 4-[1-(p-Fluorophenyl)-1H-1,2,4-triazol-5-yl]-pyridine | Active |

Migratory Inhibition Test

Rheumatoid arthritis is a chronic inflammatory disease that is characterized by the migration of lymphocytes, macrophages and polymorphonuclear leukocytes to the sites of inflammation. The migration of lymphocytes and macrophages and their multiplication in situ is one reason for the very large increase in size of the normally thin synovial membrane which encloses the joint space. This transformed synovial membrane slowly grows over the articular surfaces and causes the destruction of the articular cartilage and other connective tissue structures of the joint. One of the mechanisms for the destruction of articular cartilage by the synovium is through the release of various hydrolytic enzymes by the resident macrophages which have been immobilized and activated by migration inhibitory factor (MIF). Macrophages stimulated by MIF are termed "activated macrophages" and undergo the following changes: (a) increased glucose oxidation, (b) increased ruffling of plasma membrane and increased spreading of cells, (c) synthesis and secretion of neutral proteases, (d) release of preformed lysosomal enzymes, (e) decreased migration from a capillary tube. All these effects are associated with an inflammatory situation and it has been demonstrated that MIF is present in the synovial fluid from patients with rheumatoid arthritis. The mechanism of cartilage destruction can be pictured as follows:

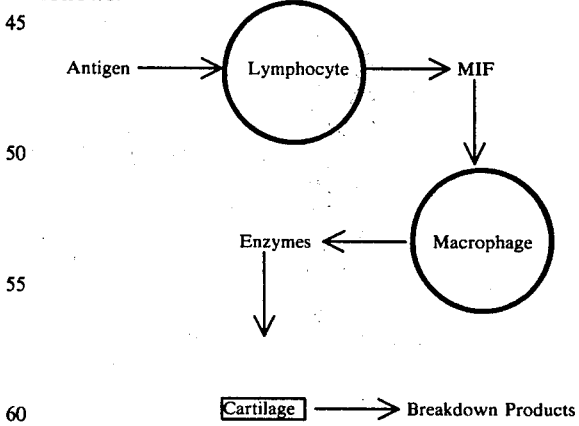

Although the postulated antigen initiating these destructive events in rheumatoid arthritis has not been discovered, the secretion of MIF by lymphocytes and the secretion of enzymes by macrophages as well as the breakdown of cartilage by macrophage enzymes has been demonstrated. Drugs that can therefore block the release of MIF by lymphocytes or the activation of macrophages by MIF may be clinically effective in retarding the destructive joint damage which occurs in rheumatoid arthritis. Drugs can be tested as MIF inhibitors by using the capillary tube migration assay as follows: Male Hartley guinea pigs, weighing between 300 and 600 grams, were injected intraperitoneally with 25 ml. of Marcal 52 Oil ® (Humble Oil Co.). Three to four days later the guinea pigs were decapitated, the peritoneum opened and 50 ml. of cold Hank's solution added to the peritoneum. The Hank's solution containing the cell suspension was then aspirated into a separatory funnel. This procedure was repeated twice. The oil phase was discarded and the cell suspension was centrifuged at 1200 r.p.m. for 10 minutes. The cells were resuspended in cold Hank's solution and centrifuged at 900 r.p.m. for 5 minutes. This procedure was repeated twice. Viability of the cells was then determined using trypan blue. Viability must be greater than 90%. The cell construction was then adjusted to give a 10% packed cell volume by the addition of the appropriate amount of Minimal Essential Medium (Earle's salts) plus 15% guinea pig serum. To the medium was added L-glutamine (2 mM), penicillin (100 U./ml.) and streptomycin (100 mcg./ml.). Capillary tubes (1.1–1.5×75 mm., Clay Adams) were filled with cells by capillary action and sealed at one end with a small plug of paraffin. These capillary tubes were centrifuged at 700–800 r.p.m. for 5 minutes to get approximately 4–5 mm. of packed cells at the closed end. The tubes were cut at the cell-fluid interface. Two packed capillary tubes were then transferred to each chamber of a Lexy culture dish (Mini-Lab Co., LLC-4002, Quebec, Canada). The capillaries were held in place using a small amount of silicone grease (Dow Corning) and a cover glass was then placed on top of the chamber, making a seal between the cover glass and the chamber using paraffin wax.

The test compound solution (c) is prepared by dissolving 10 mg. of the test compound in one ml. of absolute ethanol. A 10 μl. portion of this is transferred to 10 ml. of complete medium containing antigen. The antigen control (b) is prepared by adding 10 μl. of absolute ethanol to 10 ml. of complete medium containing antigen. The non-antigen control (a) is prepared by adding 10 μl. of absolute ethanol to 10 ml. of complete medium without antigen. Therefore, (a) contains medium +0.1% absolute ethanol; (b) contains medium +0.1% absolute ethanol+antigen; and (c) contains medium+0.1% absolute ethanol+antigen+test compound. The chamber was then filled through the passages with ether (a), (b) or (c). The passages were then sealed off using silicone. The cells were then incubated at 37° C. for 24 hours. To determine the area of cell migration out of the capillary tube onto the chamber surface, the chamber was projected onto a microscope screen, the area traced onto paper and then measured using a planimeter. The antigen inhibits the migration of macrophages by approximately 50%. Test compounds that reverse this inhibition by greater than 15% are considered active. The results of this test with typical compounds of this invention appear in Table III below.

TABLE III

| Compound | Dose mcg./ml. | Result* |
|---|---|---|
| 1-(p-Bromophenyl)-5-(p-nitrophenyl)-1H-1,2,4-triazole | 10 | Active |
| 4-(1-Phenyl-1H-1,2,4-triazol-5-yl)pyridine | 10 | Active |
| 5-(p-Aminophenyl)-1-(p-bromophenyl)-1H-1,2,4-triazole | 10 | Active |

TABLE III-continued

| Compound | Dose mcg./ml. | Result* |
|---|---|---|

*Greater than 15% reversal of inhibition, $\frac{c-b}{a-b}$, where a = cells with no addition, b = cells + antigen and c = cells + antigen + test compound.

A preferred embodiment of the present invention may be represented by the following structural formula:

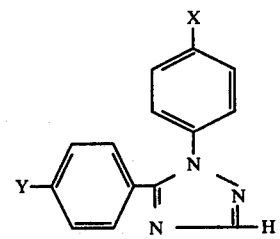

wherein X and Y are each individually selected from the group consisting of hydrogen, fluoro, chloro, bromo, nitro and amino with the proviso that X and Y may not both be hydrogen.

The invention will be described in greater detail in conjunction with the following specific examples.

EXAMPLE 1

1-Phenyl-5-(p-nitrophenyl)-1H-1,2,4-triazole

A mixture of 50.0 g. of p-nitrobenzamide, 50 ml. of N,N-dimethylformamide and 100 ml. of N,N-dimethylformamide diethylacetal is heated at 120° C. for 1.5 hours, during which time some ethanol forms and is collected through a reflux condenser. Cooling the solution produces 54.1 g. of N-(dimethylaminomethylene)-p-nitrobenzamide as colorless crystals.

To a solution of 5.4 g. of phenylhydrazine in 70 ml. of 30% aqueous acetic acid is added 10.0 g. of N-(dimethylaminomethylene)-p-nitrobenzamide. The reaction mixture is stirred at 90° C. for one hour and then cooled. The solid is collected and recrystallized from ethanol giving 9.1 g. of the desired product as colorless crystals, mp. 130°–132° C.

EXAMPLE 2

1-(p-Fluorophenyl)-5-(p-nitrophenyl)-1H-1,2,4-triazole

To a solution of 8.80 g. of 4-fluorophenylhydrazine hydrochloride in a mixture of 10.9 ml. of 5 N sodium hydroxide, 100 ml. of 30% aqueous acetic acid and 50 ml. of p-dioxane is added 10.0 g. of N-(dimethylaminomethylene)-p-nitrobenzamide. The reaction mixture is stirred and heated at 90° C. for 1.5 hours, then poured into 200 ml. of water. The solid is collected and recrystallized from ethanol, giving 10.4 g. of the desired product as yellow crystals, mp. 132°–134° C.

EXAMPLE 3

1-(p-Bromophenyl)-5-(p-nitrophenyl)-1H-1,2,4-triazole

To a solution of 12.1 g. of 4-bromophenylhydrazine hydrochloride in a mixture of 10.9 ml. of 5 N sodium hydroxide, 100 ml. of 30% aqueous acetic acid and 50 ml. of p-dioxane is added 10.0 g. of N-(dimethylaminomethylene)-p-nitrobenzamide. The procedure of Example 2 is followed, giving 12.7 g. of the desired product as tan crystals, mp. 142°–144° C.

EXAMPLE 4

3-(4H-1,2,4-Triazol-3-yl)-pyridine

A solution of 75.0 g. of nicotinamide in 150 ml. of N,N-dimethylformamide diethylacetal is heated at 120° C. for 1.5 hours during which time some ethanol is forms and is collected through a reflux condenser. Cooling the solution produces 88.0 g. of N-(dimethylaminomethylene)nicotinamide as colorless crystals.

To a solution of 3.1 g. of hydrazine hydrate in 100 ml. of acetic acid is added 10.0 g. of N-(dimethylaminomethylene)nicotinamide. The reaction mixture is stirred at 90° C. for 1.5 hours, then concentrated in vacuo to about 15 ml. The addition of 50 ml. of ether causes the desired product to precipitate as 7.8 g. of colorless crystals, mp. 169°–172° C.

EXAMPLE 5

2-[1-(p-Chlorophenyl)-1H-1,2,4-triazol-5yl]pyrazine

A solution of 15.0 g. of pyrazinamide in 40 ml. of N,N-dimethylformamide diethylacetal is heated at 120° C. for 2 hours with collection of ethanol. Cooling gives 9.9 g. of N-(dimethylaminomethylene)pyrazinecarboxamide as tan crystals.

To a solution of 12.1 g. of 4-chlorophenylhydrazine hydrochloride in a mixture of 13.5 ml. of 5 N sodium hydroxide, 100 ml. of 30% aqueous acetic acid and 50 ml. of p-dioxane is added 10.0 g. of N-(dimethylaminomethylene)pyrazinecarboxamide. The procedure of Example 2 is then followed giving 3.8 g. of the desired product as tan crystals, mp. 129°–131° C.

EXAMPLE 6

4-(1-Phenyl-1H-1,2,4-triazol-5-yl)pyridine

A 75.0 g. portion of isonicotinamide is reacted as described in Example 4 for nicotinamide, giving 86.6 g. of N-(dimethylaminomethylene)isonicotinamide as tan crystals.

To a solution of 6.9 g. of phenylhydrazine in 100 ml. of acetic acid is added 10.0 g. of N-(dimethylaminomethylene)isonicotinamide. The reaction mixture is stirred at 90° C. for 1.5 hours and then evaporated in vacuo to an orange oil. This oil is dissolved in 250 ml. of chloroform, washed with 60 ml. of saturated sodium bicarbonate solution, then with 60 ml. of water, dried over sodium sulfate and filtered. The chloroform is removed and the residue is dissolved in 60 ml. of ether. Cooling produces 8.8 g. of the desired product as tan crystals, mp. 92°–94° C.

EXAMPLE 7

{1-[p-(Difluoromethylsulfonyl)phenyl]-1H-1,2,4-triazol-5-yl}pyrazine

A reaction mixture comprising 100 g. of pyrazinamide in 270 ml. of dimethylformamide diethylacetal is heated at 120° C. for 2 hours with collection of ethanol. The mixture is cooled, the solid is collected by filtration and washed with ether giving 40.6 g. of N-(dimethylaminomethylene)pyrazine carboxamide.

A reaction mixture comprising 10.0 g. of the above product and 15.0 g. of p-(difluoromethylsulfonyl)phenylhydrazine in 100 ml. of acetic acid is stirred at 90° C. for 3 hours and concentrated in vacuo to an oil. The oil is dissolved in 250 ml. of chloroform, washed with two 100 ml. portions of water, dried over sodium sulfate and filtered. The solvent is removed and the residue is dissolved in hot ethanol. Cooling produces 7.8 g. of the desired product as tan crystals, mp. 152°–154° C.

EXAMPLE 8

1,5-Diphenyl-1H-1,2,4-triazole

A reaction mixture comprising 150 g. of benzamide in 300 ml. of dimethylformamide dimethylacetal is heated at 120° C. for 3 hours with collection of methanol. The mixture is cooled and the solid is collected and washed with ether giving 173.2 g. of N-(dimethylaminomethylene)benzamide.

A reaction mixture comprising 10.0 g. of the above product, 7.36 g. of phenylhydrazine and 100 ml. of acetic acid is reacted as described in Example 7, giving 7.1 g. of the desired product as colorless crystals, mp. 85°–87° C.

EXAMPLE 9

1-(p-Bromophenyl)-3-methyl-5-(3,4,5-trimethoxyphenyl)-1H-1,2,4-triazole

A reaction mixture comprising 100 g. of 3,4,5-trimethoxybenzamide in 200 ml. of 85% dimethylacetamide is heated at 120° C. for 2 hours with collection of methanol. The mixture is cooled, the solid is collected by filtration and recrystallized from dimethylformamide giving 88.1 g. of N-(dimethylaminoethylidene)-3,4,5-trimethoxybenzamide as light yellow crystals.

A 10.0 g. portion of the above product is added to a mixture of 9.60 g. of 4-bromophenylhydrazine hydrochloride, 8.58 ml. of 5 N sodium hydroxide, 100 ml. of 30% aqueous acetic acid and 100 ml. of p-dioxane. The reaction mixture is stirred at 90° C. for 3 hours and then evaporated in vacuo to about 30 ml. The residue is poured into 250 ml. of water and extracted with two 250 ml. portions of chloroform. The chloroform extracts are combined, washed with two 100 ml. portions of water, dried over sodium sulfate and filtered. The chloroform is removed and the residue is triturated with ether giving colorless crystals which are recrystallized from ethanol giving 8.1 g. of the desired product as colorless crystals, mp. 132°–133° C.

EXAMPLE 10

[1-(p-Nitrophenyl)-1H-1,2,4-triazol-5-yl]pyrazine 10.0 g. of portion of N-(dimethylaminomethylene)pyrazine carboxamide is added to a mixture of 10.3 g. of 4-nitrophenylhydrazine, 200 ml. of acetic acid and 50 ml. of p-dioxane. The mixture is heated at 90° C. for 5 hours and evaporated to dryness in vacuo. The residue is recrystallized from ethanol giving 9.0 g. of the desired product as tan crystals, mp. 188°–189° C.

EXAMPLE 11

5-(p-Aminophenyl)-1-(p-bromophenyl)-1H-1,2,4-triazole

A mixture of 9.0 g. of 1-(p-bromophenyl)-5-(p-nitrophenyl)-1H-1,2,4-triazole, 18.0 g. of sodium hydrosulfite, 40 ml. of water and 150 ml. of acetone is stirred at room temperature overnight. The acetone is removed in vacuo and the residue is extracted with hot chloroform. Cooling produces 2.1 g. of the desired product as pale yellow crystals, mp. 128°–130° C.

EXAMPLE 12

4-[1-(p-Fluorophenyl)-1H-1,2,4-triazol-5-yl]pyridine

A 6.0 g. portion of N-(dimethylaminomethylene)isonicotinamide is added to a mixture prepared by adding 6.05 g. of p-fluorophenylhydrazine hydrochloride to 80 ml. of 30% aqueous acetic acid, 40 ml. of p-dioxane and 7.5 ml. of 5 N sodium hydroxide. The mixture is heated to reflux for 1.5 hours, poured into water and allowed to stand overnight. Extraction with ether gives a dark solid which is recrystallized from acetone-hexane giving 1.7 g. of the desired product, mp. 114°–115° C.

EXAMPLE 13

5-(p-Aminophenyl)-1-(p-fluorophenyl)-1H-1,2,4-triazole

A mixture of 9.0 g. of 1-(p-fluorophenyl)-5-(p-nitrophenyl)-1H-1,2,4-triazole, 18.0 g. of sodium hydrosulfite, 40 ml. of water and 150 ml. of acetone is stirred at room temperature for ½ hour. The acetone is removed in vacuo and the residue extracted with hot chloroform. Cooling produces 1.1 g. of the desired product as off-white crystals, mp. 128°–130° C.

EXAMPLE 14

1-(p-Fluorophenyl)-5-[p-[(dimethylaminomethylene)amino]phenyl]-1H-1,2,4-triazole A solution of 5.0 g. of 5-(p-aminophenyl)-1-(p-fluorophenyl)-1H-1,2,4-triazole in 20 ml. of dimethylformamide dimethylacetal is heated to reflux for 1.5 hours while the methanol formed is collected by distillation. The reaction mixture is cooled, 15 ml. of ether is added and the mixture is cooled further, giving 5.5 g. of the desired product, mp. 159°–161° C.

EXAMPLE 15

2-Cyano-4'-[1-(p-fluorophenyl)-1H-1,3,4-triazol-5-yl]acetanilide

A solution of 3.5 ml. of phosphorus trichloride in 25 ml. of acetonitrile is added dropwise to a stirred suspension of 19.0 g. of 5-(p-aminophenyl)-1-(p-fluorophenyl)-1H-1,2,4-triazole in a mixture of 15.6 ml. of triethylamine, 6.35 g. of cyanoacetic acid and 200 ml. of acetonitrile at room temperature over a period of one hour. The mixture is heated to boiling, giving a clear solution and kept at 90° C. for 2.5 hours. The suspension is filtered hot through diatomaceous earth. The filtrate is heated to boiling, 250 ml. of hot water is added and the solution is slowly cooled to 5° C. A 400 ml. portion of water is added and the solid is collected and recrystallized from ethanol giving the desired product as 19.0 g. of cream crystals, mp. 223°–225° C.

EXAMPLE 16

5-(p-Aminophenyl)-1-(p-chlorophenyl)-1H-1,2,4-triazole

To a solution of 38.9 g. of 4-chlorophenylhydrazine hydrochloride in a mixture of 400 ml. of 30% aqueous acetic acid, 43.6 ml. of 5 N sodium hydroxide and 200 ml. of p-dioxane is added 40.0 g. of N-(dimethylaminomethylene)-p-nitrobenzamide. The mixture is stirred and heated at 90° C. for 1.5 hours, concentrated in vacuo to about 350 ml. and 350 ml. of water is added. The mixture is refrigerated overnight and the solid is collected, washed with water and recrystallized from 600 ml. of ethanol giving 48.6 g. of 1-(p-chlorophenyl)-5-(p-nitrophenyl)-1H-1,2,4-triazole as cream crystals.

To a solution of 40.0 g. of the above product in 320 ml. of p-dioxane at 80° C. is added a hot (70° C.) solution of 74.4 g. of sodium sulfide nonahydrate in 320 ml. of water. The mixture is stirred at 80° C. for 45 minutes, cooled and poured into one liter of ice-water. The solid is collected by filtration and recrystallized from chloroform-hexane giving 23.7 g. of the desired product as colorless crystals, mp. 150°–152° C.

EXAMPLE 17

5-(p-Fluorophenyl)-1-(p-nitrophenyl)-1H-1,2,4-triazole

A mixture comprising 116 ml. of dimethylformamide dimethylacetal, 62.0 ml. of dimethylformamide and 60.0 g. of p-fluorobenzamide is stirred and heated at 90°–120° C. for 3 hours with collection of methanol. The mixture is cooled in an ice bath giving a solid which is collected by filtration, washed with three 75 ml. portions of ether and dried, giving 53.0 g. of N-(dimethylaminomethylene)-p-fluorobenzamide.

A 12.4 g. portion of the above product in 50 ml. of p-dioxane is added to a mixture of 16.7 g. of 4-nitrophenylhydrazine in 75 ml. of p-dioxane, 105 ml. of water and 45 ml. of glacial acetic acid. This mixture is heated to 90° C., 250 ml. of dimethylformamide is added and the solution is heated at 90° C. for 1.5 hours. The solution is concentrated in vacuo at 80° C. to 300 ml. and poured into 1200 ml. of water with stirring. The solid is collected by filtration, washed with water, then two 50 ml. portions of ether and recrystallized twice from ethanol giving the desired product as 6.7 g. of brown crystals, mp. 151°–154° C.

EXAMPLE 18

1-(p-Aminophenyl)-5-(p-fluorophenyl)-1H-1,2,4-triazole

A 5.0 g. portion of 5-(p-fluorophenyl)-1-(p-nitrophenyl)-1H-1,2,4-triazole in 42 ml. of dioxane is added to 9.9 g. of sodium sulfide nonahydrate in 42 ml. of water and the mixture is stirred and heated at reflux (90° C.) for 1.5 hours. The solution is cooled and poured into 300 ml. of ice and water with stirring. The solid is collected by filtration, dried, recrystallized from 30 ml. of acetonitrile, washed with ether and dried giving 2.6 g. of the desired product as tan crystals, mp. 147°–150° C.

EXAMPLE 19

N'-[p-[5-(p-Fluorophenyl)-1H-1,2,4-triazol-1-yl]phenyl]-N,N-dimethylformamidine A 1.7 g. portion of 1-(p-aminophenyl)-5-(p-fluorophenyl)-1H-1,2,4-triazole is gently refluxed in a mixture of 5.0 ml. of dimethylformamide dimethylacetal and 2.5 ml. of dimethylformamide. Heating is continued for 1.5 hours, then the mixture is evaporated under high vacuum (70° C.) to a brown oil. This oil is triturated with 50 ml. of ether. The solid is collected by filtration, dried and recrystallized from 25 ml. of hot cyclohexane, giving 1.1 g. of the desired product as a light tan solid, mp. 90°–93° C.

EXAMPLE 20

N'-[p-5-(p-Bromophenyl)-1H-1,2,4-triazol-1-yl]-N,N-dimethylformamidine

A 24.8 g. of portion of p-bromobenzamide in 33.0 ml. of dimethylformamide dimethylacetal and 200 ml. of dimethylformamide is heated at 120° C. until evolution of methanol ceases (2 hours). The mixture is cooled and then evaporated under high vacuum to a gum which is triturated with ether. The resulting crystals are collected, washed with ether, dried and then recrystallized from 150 ml. of ethanol at 0° C. giving 21.8 g. of N-(dimethylaminomethylene)-p-bromobenzamide as yellow crystals.

A 12.7 g. portion of the above product in 50 ml. of p-dioxane is added to a mixture of 11.7 g. of p-nitrophenylhydrazine, 75 ml. of p-dioxane, 45 ml. of acetic acid and 105 ml. of water and heated at 90° C. for 2 hours. A 250 ml. portion of p-dioxane and 100 ml. of dimethylformamide are added to effect solution. The mixture is cooled and poured into 1200 ml. of water. The precipitate is collected by filtration, washed with water, dried and recrystallized from ethanol giving 6.75 g. of 5-(p-bromophenyl)-1-(p-nitrophenyl)-1H-1,2,4-triazole as orange crystals.

An 8.1 g. portion of sodium sulfide nonahydrate in 35 ml. of water is heated to 60° C. and added to a solution of 5.5 g. of the above triazole in 35 ml. of p-dioxane at 90° C. The mixture is cooled and poured into 300 ml. of water with stirring. The solid is collected by filtration, washed with water, dried and recrystallized from chloroform:cyclohexane (1:1) giving 1.9 g. of 1-(p-aminophenyl)-5-(p-bromophenyl)-1H-1,2,4-triazole as a brown solid.

A 1.6 g. portion of the above amine in 5 ml. of dimethylformamide dimethylacetal and 2.5 ml. of dimethylformamide is heated at 90° C. for 1.5 hours, cooled and evaporated under high vacuum to a brown oil. This oil is triturated with 30 ml. of ether. The resulting solid is collected by filtration, dried and recrystallized from 25 ml. of chloroform:cyclohexane (1:1), giving 1.30 g. of the desired product as a tan solid, mp. 140°–144° C.

EXAMPLE 21

1-(p-Aminophenyl) -5-phenyl-1H-1,2,4-triazole

A reaction mixture comprising 22.4 g. of N-(dimethylaminomethylene)benzamide in 100 ml. of p-dioxane is added to a mixture of 23.5 g. of p-nitrophenylhydrazine in 150 ml. of p-dioxane, 80 ml. of acetic acid and 210 ml. of water. The mixture is stirred and heated at 90°–95° C. for 2 hours with the addition of 250 ml. of dimethylformamide to effect solution. The mixture is cooled and poured into one liter of ice-water producing a brown oil. This oil solidifies, is collected, dried and recrystallized from ethanol giving 6.7 g. of 1-(p-nitrophenyl)5-phenyl-1H-1,2,4-triazole.

A 6.0 g. portion of the above triazole in 55 ml. of p-dioxane is stirred and boiled at 90°–95° C. together with a mixture of 12.7 g. of sodium sulfide nonahydrate in 55 ml. of water. After 2 hours, the mixture is cooled and poured into 400 ml. of water. The solid is collected by filtration, washed with water, dried and recrystallized from chloroform-hexane, giving 750 mg. of the desired product as cream colored crystals, mp. 161°–163° C.

EXAMPLE 22

N,N-Dimethyl-N'-[p-(5-phenyl-1H-1,2,4-triazol-1-yl)phenyl]formamidine

A 1.5 g. portion of 1-(p-aminophenyl)-5-phenyl-1H-1,2,4-triazole in 10.0 ml. of dimethylformamide dimethylacetal and 4.0 ml. of dimethylformamide is heated at 90°–95° C. for 1.5 hours. The solution is concentrated to 10 ml., cooled and then evaporated at 60° C. to an oil. This oil is triturated with 50 ml. of ether. The solid is collected by filtration and recrystallized from chloroform-hexane giving 670 mg. of the desired product as yellow plates, mp. 109°–111° C.

EXAMPLE 23

1-(o-Fluorophenyl)-5-(p-nitrophenyl)-1H-1,2,4-triazole

A 25.0 g. portion of o-fluorophenylhydrazine hydrochloride is dissolved in 150 ml. of p-dioxane with warming and 31.0 ml. of 5 N sodium hydroxide is added. After solution is complete, 80 ml. of glacial acetic acid and 210 ml. of water are added followed by 28.1 g. of N-(dimethylaminomethylene)-p-nitrobenzamide in 100 ml. of warm p-dioxane. This reaction mixture is heated at 90°–95° C. for 1.5 hours, then cooled and poured into 1500 ml. of water. The solid is collected by filtration, washed with water, dried and crystallized from 200 ml. of ethanol, giving 13.9 g. of the desired product as a tan solid, mp. 143°–145° C.

EXAMPLE 24

5-(p-Aminophenyl)-1-(o-fluorophenyl)-1H-1,2,4-triazole

An 11.9 g. portion of 1-(o-fluorophenyl)-5-(p-nitrophenyl)-1H-1,2,4-triazole and 25.4 g. of sodium sulfide nonahydrate in a mixture of 110 ml. of p-dioxane and 110 ml. of water is heated at 90°–95° C. for 1.5 hours. The solution is cooled, poured into one liter of water and allowed to stand overnight. The solid is collected by filtration, washed with water and dried. This solid is taken up in the minimum amount of warm chloroform, cooled, dried over magnesium sulfate and filtered through diatomaceous earth. Hexane is added until the mixture becomes cloudy and deposits crystals. After 2 hours, the solid is collected by filtration, washed with ether, dried and recrystallized from chloroform-hexane giving the desired product as yellow crystals, mp. 139°–141° C.

We claim:

1. A compound selected from the group consisting of those of the formula:

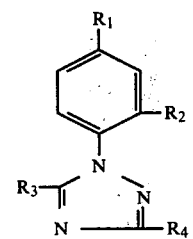

wherein $R_1$ and $R_2$ are each individually selected from the group consisting of hydrogen, fluoro, chloro, bromo, nitro, amino and dimethylaminomethyleneamino; $R_3$ is selected from the group consisting of 3,4,5-trimethoxyphenyl and moieties of the formula:

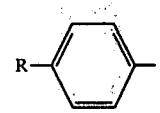

wherein R is hydrogen, fluoro, chloro, bromo, nitro, amino or dimethylaminomethyleneamino with the proviso that when R is hydrogen then $R_1$ and $R_2$ may not both be hydrogen; and $R_4$ is hydrogen or methyl; and the pharmaceutically acceptable acid addition salts thereof.

2. The compound according to claim 1 wherein $R_1$ is fluoro, $R_3$ is 4-nitrophenyl, and $R_2$ and $R_4$ are hydrogen.

3. The compound according to claim 1 wherein $R_1$ is bromo, $R_3$ is 4-nitrophenyl, and $R_2$ and $R_4$ are hydrogen.

4. The compound according to claim 1 wherein $R_1$ is bromo, $R_3$ is 4-aminophenyl, and $R_2$ and $R_4$ are hydrogen.

5. The compound according to claim 1 wherein $R_1$ is fluoro, $R_3$ is 4-aminophenyl, and $R_2$ and $R_4$ are hydrogen.

6. The compound according to claim 1 wherein $R_3$ is 4-nitrophenyl, and $R_1$, $R_2$ and $R_4$ are hydrogen.

7. The compound according to claim 1 wherein $R_1$ is chloro, $R_3$ is 4-aminophenyl, and $R_2$ and $R_4$ are hydrogen.

8. The compound according to claim 1 wherein $R_2$ is fluoro, $R_3$ is 4-nitrophenyl, and $R_1$ and $R_4$ are hydrogen.

9. The compound according to claim 1 wherein $R_1$ is fluoro, $R_3$ is 4-dimethylaminomethyleneaminophenyl, and $R_2$ and $R_4$ are hydrogen.

* * * * *